US012582653B2

(12) United States Patent
Zhao et al.

(10) Patent No.: US 12,582,653 B2
(45) **Date of Patent: *Mar. 24, 2026**

(54) METHOD FOR TREATING IDIOPATHIC PULMONARY FIBROSIS

(71) Applicant: BEIJING TIDE PHARMACEUTICAL CO., LTD., Beijing (CN)

(72) Inventors: Yanping Zhao, Beijing (CN); Hongjun Wang, Beijing (CN); Yuanyuan Jiang, Beijing (CN); Weiting Zhong, Beijing (CN); Jing Zhao, Beijing (CN); Jing Li, Beijing (CN); Weina Liu, Beijing (CN); Liying Zhou, Beijing (CN); Yanan Liu, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 903 days.

This patent is subject to a terminal disclaimer.

(21) Appl. No.: 17/621,719

(22) PCT Filed: Jun. 24, 2020

(86) PCT No.: PCT/CN2020/097881

§ 371 (c)(1),
(2) Date: Dec. 22, 2021

(87) PCT Pub. No.: WO2020/259528

PCT Pub. Date: Dec. 30, 2020

(65) Prior Publication Data

US 2022/0233538 A1 Jul. 28, 2022

(51) Int. Cl.
*A61K 31/506* (2006.01)
*A61P 11/00* (2006.01)

(52) U.S. Cl.
CPC ............ *A61K 31/506* (2013.01); *A61P 11/00* (2018.01)

(58) Field of Classification Search
CPC ................................ A61K 3/506; A61P 11/00
See application file for complete search history.

(56) References Cited

U.S. PATENT DOCUMENTS

| | | | | |
|---|---|---|---|---|
| 11,390,609 B2 * | 7/2022 | Zhao | .................... | C07D 471/10 |
| 2018/0170939 A1 * | 6/2018 | Accetta | .................... | A61P 11/06 |

(Continued)

FOREIGN PATENT DOCUMENTS

| | | |
|---|---|---|
| EP | 3647311 | 5/2020 |
| JP | 2018506571 | 3/2018 |

(Continued)

OTHER PUBLICATIONS

National Clinical Guideline Centre (UK). 2013. Diagnosis and Management of Suspected Idiopathic Pulmonary Fibrosis: Idiopathic Pulmonary Fibrosis [Internet]. Chapter 11, Pharmacological interventions. Accessed Oct. 18, 2024. Available from: <<https://www.ncbi.nlm.nih.gov/books/NBK327927/>> (Year: 2013).*

(Continued)

*Primary Examiner* — Kamal A Saeed
*Assistant Examiner* — Jalisa Holmes Ferguson
(74) *Attorney, Agent, or Firm* — Robin L. Teskin; Baker, Donelson, Bearman, Caldwell & Berkowitz PC

(57) ABSTRACT

A method for preventing, alleviating and/or treating idiopathic pulmonary fibrosis, which comprises administering an effective amount of a compound represented by formula (I), or a pharmaceutically acceptable salt, ester, stereoisomer, polymorph, solvate, N-oxide, isotope-labeled compound, metabolite or prodrug thereof to an individual in need thereof.

(Continued)

(I)

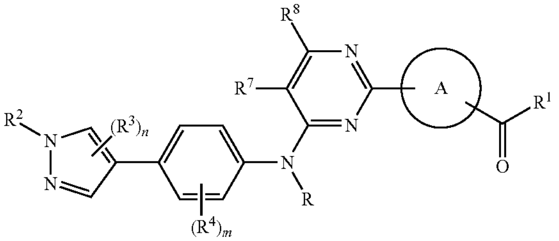

13 Claims, 6 Drawing Sheets

(56) References Cited

U.S. PATENT DOCUMENTS

2019/0010143 A1 1/2019 Zhao et al.
2019/0276440 A1* 9/2019 Zhao .................... C07D 453/02

FOREIGN PATENT DOCUMENTS

| | | |
|---|---|---|
| WO | 2016138335 | 9/2016 |
| WO | 2019000682 | 9/2017 |
| WO | 2019001572 | 1/2019 |

OTHER PUBLICATIONS

Shimizu Y, Dobashi K, Sano T, Yamada M. ROCK activation in lung of idiopathic pulmonary fibrosis with oxidative stress. International journal of immunopathology and pharmacology. Jan. 2014;27(1):37-44.

Yu Yuanxun. Signal Transduction Pathways and Targeted Therapy of Diseases in China. Anhui Science and Technology Publishing House, May 31, 2013, p. 242.

Chen Linxi, et al., Cell Signal Transduction Pharmacology and Clinic, People's Military Medical Press, Oct. 31, 2014, p. 174.

* cited by examiner represents P<0.0001, compared to the normal group;
* represents P<0.05, compared to the vehicle group;
** represents P<0.01, compared to the vehicle group.

represents P<0.0001, compared to the normal group;
**** represents P<0.0001, compared to the vehicle group.

*p<0.05, p<0.01, *p<0.001, *p<0.001, **p<0.0001, compared to the model group.
A-Normal group; B-Model group; C-Pirfenidone administration group;
D-Nintedanib administration group; E-Compound 007 (30 mpk) administration group;
F-Compound 007 (100 mpk) administration group;
G-Compound 007 (300 mpk) administration group.

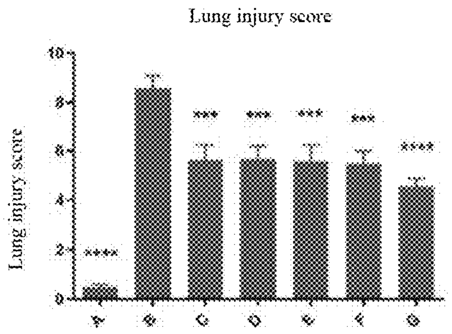

*p<0.001, **p<0.0001, compared to the model group.
A-Normal group; B-Model group; C-Pirfenidone administration group;
D-Nintedanib administration group; E-Compound 007 (30 mpk) administration group;
F-Compound 007 (100 mpk) administration group;
G-Compound 007 (300 mpk) administration group.

FIG.7B

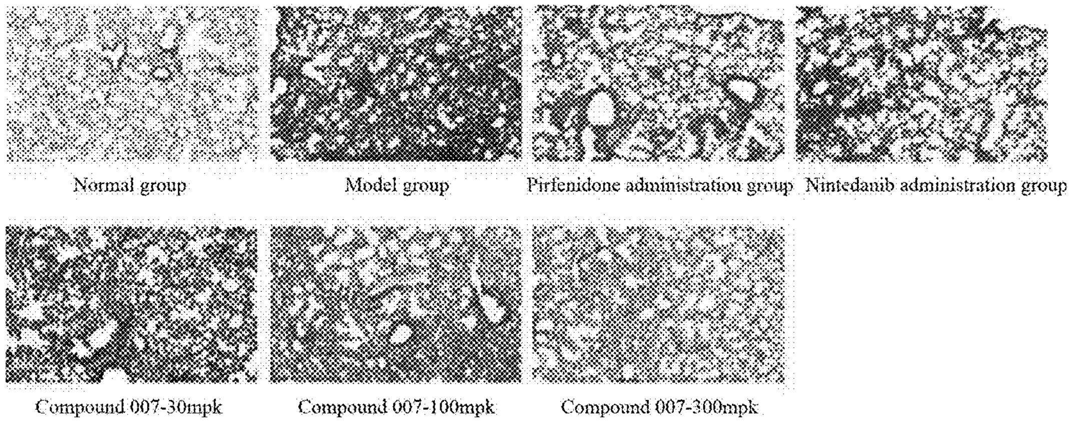

FIG.8A

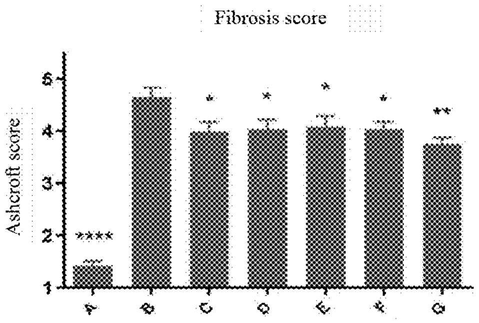

*p<0.05, **p<0.01, compared to the model group.
A-Normal group; B-Model group; C-Pirfenidone administration group;
D-Nintedanib administration group; E-Compound 007 (30 mpk) administration group;
F-Compound 007 (100 mpk) administration group;
G-Compound 007 (300 mpk) administration group.

FIG.8B

METHOD FOR TREATING IDIOPATHIC PULMONARY FIBROSIS

CROSS-REFERENCE TO RELATED APPLICATIONS

This application is a U.S. National Phase of Int'l Appl. No. PCT/CN2020/097881, filed Jun. 24, 2020, which claims priority to Int'l Appl. No. PCT/CN2019/092675, filed Jun. 25, 2019.

FIELD OF THE INVENTION

The present disclosure falls within the field of biological medicine, and specifically relates to a method for preventing, alleviating and/or treating idiopathic pulmonary fibrosis, comprising administering to a subject in need thereof an effective amount of a compound of the present application or a pharmaceutically acceptable salt, ester, stereoisomer, polymorph, solvate, N-oxide, isotopically labeled compound, metabolite or prodrug thereof.

BACKGROUND OF THE INVENTION

Idiopathic pulmonary fibrosis (IPF) is a chronic, progressive fibrotic disorder in the lower respiratory tract of unknown etiology, with an increasing incidence. The disease is characterized by progressive accumulation of extracellular matrix within the interstitium. Increasing fibrosis leads to decreasing lung function and patients usually die of respiratory failure or other complications within three years of biopsy-confirmed diagnosis. Historically, corticosteroids (e.g., prednisolone) in combination with immunosuppressives (e.g., azathioprine) and/or N-acetylcysteine, have been advocated as a therapeutic strategy for IPF. Another drug which has been approved for the treatment of IPF in Japan, Europe, India and Canada is Pirfenidone, which has combined anti-inflammatory, antioxidant and anti-fibrotic actions in experimental models of IPF. It is the only drug for which an improved progression-free survival time has been observed. At present, there is no scientific evidence to suggest that current therapeutic strategies can reverse fibrosis in IPF; the goal of most therapies is to reduce the rate of disease progression and/or prevent disease development.

It is clear that better and more effective treatments for IPF are still needed.

SUMMARY OF THE INVENTION

In one aspect, the present disclosure provides a method for preventing, alleviating and/or treating idiopathic pulmonary fibrosis, comprising administering to a subject in need thereof an effective amount of a compound of Formula (I) or a pharmaceutically acceptable salt, ester, stereoisomer, polymorph, solvate, N-oxide, isotopically labeled compound, metabolite or prodrug thereof:

(I)

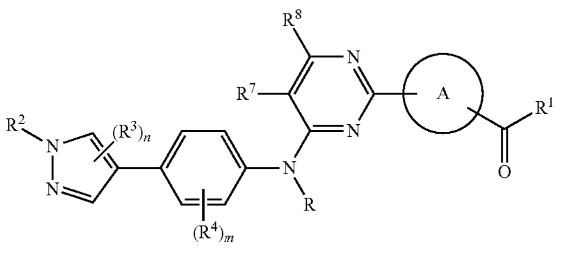

wherein:

ring A is

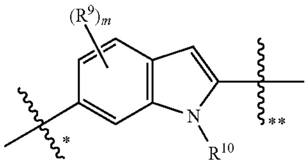

or

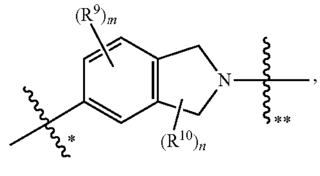

, the above group is attached to the pyrimidine ring at either of the two positions labeled * or **, and is attached to the carbonyl group at the other position;

R is selected from the group consisting of H and $C_{1-6}$ alkyl;

$R^1$ is

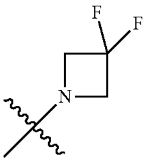

or

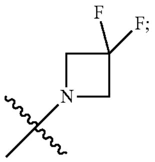

;

$R^2$ is selected from the group consisting of H and $C_{1-6}$ alkyl;

$R^3$, $R^4$, $R^7$ and $R^8$, at each occurrence, are each independently selected from the group consisting of H, halogen, —$NR^5R^6$, —OH, $C_{1-6}$ alkyl and —$OR^5$;

$R^9$ and $R^{10}$, at each occurrence, are each independently selected from the group consisting of H, halogen, $C_{1-6}$ alkyl, $C_{2-6}$ alkenyl, $C_{3-10}$ cyclic hydrocarbyl, 3-10-membered heterocyclyl, $C_{6-10}$ aryl, 5-14-membered heteroaryl, $C_{6-12}$ aralkyl, —C(═O)$R^5$ and —$C_{1-6}$ alkylene-O(P═O)$(OH)_2$;

the above alkylene, alkyl, alkenyl, cyclic hydrocarbyl, heterocyclyl, aryl, heteroaryl and aralkyl, at each occurrence, are each optionally substituted with one or more substituents independently selected from the group consisting of halogen, $C_{1-6}$ alkyl and —$OR^5$;

$R^5$ and $R^6$, at each occurrence, are each independently selected from the group consisting of H, $C_{1-6}$ alkyl, $C_{3-10}$ cyclic hydrocarbyl, 3-10-membered heterocyclyl, $C_{6-10}$ aryl, 5-14-membered heteroaryl and $C_{6-12}$ aralkyl;

m, at each occurrence, is each independently an integer of 0, 1, 2 or 3; and n, at each occurrence, is each independently an integer of 0, 1 or 2.

In another aspect, the present disclosure provides use of the compound of Formula (I) or a pharmaceutically acceptable salt, ester, stereoisomer, polymorph, solvate, N-oxide, isotopically labeled compound, metabolite or prodrug thereof in the manufacture of a medicament for preventing, alleviating and/or treating idiopathic pulmonary fibrosis.

In yet another aspect, the present disclosure provides the compound of Formula (I) or a pharmaceutically acceptable salt, ester, stereoisomer, polymorph, solvate, N-oxide, isotopically labeled compound, metabolite or prodrug thereof for use of preventing, alleviating and/or treating idiopathic pulmonary fibrosis.

BRIEF DESCRIPTION OF THE DRAWINGS

FIG. 7B shows the lung injury score of the animals in each group after the administration in Example 3.

FIG. 8A shows representative Masson Trichome staining pathological photos of each group in Example 3.

FIG. 8B shows the lung tissue fibrosis score of the animals in each group after the administration in Example 3.

DETAILED DESCRIPTION OF THE INVENTION

Definition

Figure 1A:
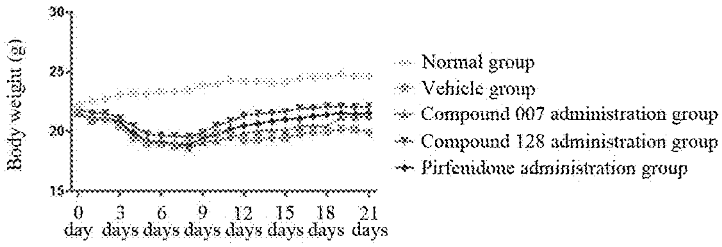
FIG. 1A shows the body weight change of the animals in each group during the test period in Example 2 (Day 0 is the first day of bleomycin induction).

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

As used herein, the term "alkylene" refers to a saturated divalent hydrocarbyl, preferably refers to a saturated divalent hydrocarbyl having 1, 2, 3, 4, 5 or 6 carbon atoms, e.g., methylene, ethylene, propylene or butylene.

As used herein, the term "alkyl" is defined as a linear or branched saturated aliphatic hydrocarbon. In some embodiments, alkyl has 1-12, e.g., 1-6, carbon atoms. For example, as used herein, the term "$C_{1-6}$ alkyl" refers to a linear or branched group having 1-6 carbon atoms (such as methyl, ethyl, n-propyl, isopropyl, n-butyl, isobutyl, sec-butyl, tert-butyl, n-pentyl, isopentyl, neopentyl, or n-hexyl), which is optionally substituted with one or more (e.g., 1 to 3) suitable substituents such as halogen (in which case the group may be referred to as "haloalkyl") (e.g., $CH_2F$, $CHF_2$, $CF_3$, $CCl_3$, $C_2F_5$, $C_2Cl_5$, $CH_2CF_3$, $CH_2Cl$ or $—CH_2CH_2CF_3$ etc.). The term "$C_{1-4}$ alkyl" refers to a linear or branched aliphatic hydrocarbon chain having 1-4 carbon atoms (i.e., methyl, ethyl, n-propyl, isopropyl, n-butyl, isobutyl, sec-butyl or tert-butyl).

As used herein, the term "alkenyl" refers to a linear or branched monovalent hydrocarbyl having a double bond and 2-6 carbon atoms ("$C_{2-6}$ alkenyl"). The alkenyl is e.g., vinyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl and 4-methyl-3-pentenyl. When the compound of the present invention contains an alkenylene group, the compound may exist as the pure E (entgegen) form, the pure Z (zusammen) form, or any mixture thereof.

As used herein, the term "alkynyl" refers to a monovalent hydrocarbyl containing one or more triple bond, and preferably having 2, 3, 4, 5 or 6 carbon atoms, e.g., ethynyl or propynyl.

As used herein, the term "cycloalkyl" refers to a saturated monocyclic or polycyclic (e.g., bicyclic) hydrocarbon ring (e.g., monocyclic, such as cyclopropyl, cyclobutyl, cyclopentyl, cyclohexyl, cycloheptyl, cyclooctyl, or cyclononyl, or bicyclic, including spiro, fused or bridged cyclic system (such as bicyclo[1.1.1]pentyl, bicyclo[2.2.1]heptyl, bicyclo[3.2.1]octyl or bicyclo[5.2.0]nonyl, or decahydronaphthalene etc.)), which is optionally substituted with one or more (e.g., 1 to 3) suitable substituents. The cycloalkyl has 3 to 15 carbon atoms. For example, the term "$C_{3-6}$ cycloalkyl" refers to a saturated monocyclic or polycyclic (e.g., bicyclic) hydrocarbon ring having 3 to 6 ring forming carbon atoms (e.g., cyclopropyl, cyclobutyl, cyclopentyl, or cyclohexyl), which is optionally substituted with one or more (e.g., 1 to 3) suitable substituents, e.g., methyl substituted cyclopropyl.

As used herein, the terms "cyclic hydrocarbylene", "cyclic hydrocarbyl" and "hydrocarbon ring" refer to a saturated (i.e., "cycloalkylene" and "cycloalkyl") or unsaturated (i.e., having one or more double and/or triple bonds in the ring) monocyclic or polycyclic hydrocarbon ring having e.g., 3-10 (suitably having 3-8, and more suitably having 3-6) ring carbon atoms, including but not limited to cyclopropyl(ene) (ring), cyclobutyl(ene) (ring), cyclopentyl(ene) (ring), cyclohexyl(ene) (ring), cycloheptyl(ene) (ring), cyclooctyl(ene) (ring), cyclononyl(ene) (ring), cyclohexenyl (ene) (ring), and the like.

As used herein, the terms "heterocyclyl", "heterocyclylene" and "heterocycle" refer to a saturated (i.e., heterocycloalkyl) or partially unsaturated (i.e., having one or more double and/or triple bonds in the ring) cyclic group having e.g., 3-10 (suitably having 3-8, and more suitably having 3-6) ring atoms, wherein at least one ring atom is a heteroatom selected from the group consisting of N, O and S, and the remaining ring atoms are C. For example, "3- to 10-membered heterocyclyl(ene)" of "3- to 10-membered heterocycle" refers to saturated or partially unsaturated heterocyclyl(ene) or heterocycle having 2-9 (e.g., 2, 3, 4, 5, 6, 7, 8 or 9) ring carbon atoms and one or more (e.g., 1, 2, 3, or 4) heteroatoms independently selected from the group consisting of N, O and S. Examples of heterocyclylene, heterocyclyl and heterocycle include, but are not limited to oxiranyl(ene), aziridinyl(ene), azetidinyl(ene), oxetanyl (ene), tetrahydrofuranyl(ene), dioxolinyl(ene), pyrrolidinyl (ene), pyrrolidonyl(ene), imidazolidinyl(ene), pyrazolidinyl (ene), pyrrolinyl(ene), tetrahydropyranyl(ene), piperidinyl (ene), morpholinyl(ene), dithianyl(ene), thiomorpholinyl (ene), piperazinyl(ene) or trithianyl(ene). Said group also encompasses a bicyclic system, including a spiro, fused, or bridged system (e.g., 8-azaspiro[4.5]decane, 3,9-diazaspiro [5.5]undecane, 2-azabicyclo[2.2.2]octane, etc.). Heterocyclylene, heterocyclyl and heterocycle may optionally be substituted with one or more (e.g., 1, 2, 3 or 4) suitable substituents.

As used herein, the terms "aryl(ene)" and "aromatic ring" refer to an all-carbon monocyclic or fused-ring polycyclic aromatic group having a conjugated n electron system. For example, as used herein, the terms "$C_{6-10}$ aryl(ene)" and "$C_{6-10}$ aromatic ring" refer to an aromatic group containing 6 to 10 carbon atoms, such as phenyl(ene) (benzene ring) or naphthyl(ene) (naphthalene ring). Aryl(ene) or aromatic ring is optionally substituted with one or more (such as 1 to 3) suitable substituents (e.g., halogen, —OH, —CN, —$NO_2$, and $C_{1-6}$ alkyl, etc.).

As used herein, the terms "heteroaryl(ene)" and "heteroaromatic ring" refer to a monocyclic, bicyclic or tricyclic aromatic ring system having 5, 6, 8, 9, 10, 11, 12, 13 or 14 ring atoms, particularly 1 or 2 or 3 or 4 or 5 or 6 or 9 or 10 carbon atoms, and containing at least one heteroatom (such as O, N, or S), which can be same to different. Moreover, in each case, it can be benzo-fused. In particular, "heteroaryl (ene)" or "heteroaromatic ring" is selected from the group consisting of thienyl(ene), furyl(ene), pyrrolyl(ene), oxazolyl(ene), thiazolyl(ene), imidazolyl(ene), pyrazolyl(ene), isoxazolyl(ene), isothiazolyl(ene), oxadiazolyl(ene), triazolyl(ene), thiadiazolyl(ene) etc., and benzo derivatives thereof; or pyridinyl(ene), pyridazinyl(ene), pyrimidinyl (ene), pyrazinyl(ene), triazinyl(ene), etc., and benzo derivatives thereof.

As used herein, the term "aralkyl" preferably means aryl or heteroaryl substituted alkyl, wherein aryl, heteroaryl and alkyl are as defined herein. Normally, the aryl group may have 6-14 carbon atoms, the heteroaryl group may have 5-14 ring atoms, and the alkyl group may have 1-6 carbon atoms. Exemplary aralkyl group includes, but is not limited to, benzyl, phenylethyl, phenylpropyl, phenylbutyl.

As used herein, the term "halo" or "halogen" are defined to include F, Cl, Br, or I.

As used herein, the term "nitrogen containing heterocycle" refers to a saturated or unsaturated monocyclic or bicyclic group having 2, 3, 4, 5, 6, 7, 8, 9, 10, 11, 12 or 13 carbon atoms and at least one nitrogen atom in the ring, which may further optionally comprise one or more (e.g., one, two, three or four) ring members selected from the group consisting of N, O, C═O, S, S═O and S(═O)2. The nitrogen containing heterocycle is attached to the rest of the molecule through the nitrogen atom and any other ring atom in said nitrogen containing heterocycle. The nitrogen containing heterocycle is optionally benzo-fused, and is preferably attached to the rest of the molecule through the nitrogen atom in said nitrogen containing heterocycle and any carbon atom in the fused benzene ring.

The term "substituted" means that one or more (e.g., one, two, three, or four) hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent.

If substituents are described as being "independently selected" from a group, each substituent is selected independent of the other(s). Each substituent therefore may be identical to or different from the other substituent(s).

As used herein, the term "one or more" means one or more than one (e.g., 2, 3, 4, 5 or 10) as reasonable.

As used herein, unless specified, the point of attachment of a substituent can be from any suitable position of the substituent.

When a bond to a substituent is shown to cross a bond connecting two atoms in a ring, then such substituent may be bonded to any of the ring-forming atoms in that ring that are substitutable.

The present invention also includes all pharmaceutically acceptable isotopically labeled compounds, which are identical to those of the present invention except that one or more atoms are replaced by an atom having the same atomic number, but an atomic mass or mass number different from the atomic mass or mass number which predominates in nature. Examples of isotopes suitable for inclusion in the compound of the present invention include, but are not limited to, isotopes of hydrogen, such as $^{2}H$, $^{3}H$; carbon, such as $^{11}C$, $^{13}C$, and $^{14}C$; chlorine, such as $^{36}Cl$; fluorine, such as $^{18}F$; iodine, such as $^{123}I$ and $^{125}I$; nitrogen, such as $^{13}N$ and $^{15}N$; oxygen, such as $^{15}O$, $^{17}O$, and $^{18}O$; phosphorus, such as $^{32}P$; and sulfur, such as $^{35}S$. Certain isotopically labeled compounds of the present invention, for example those incorporating a radioactive isotope, are useful in drug and/or substrate tissue distribution studies (e.g., assays). The radioactive isotopes tritium, i.e., $^{3}H$, and carbon-14, i.e., $^{14}C$, are particularly useful for this purpose in view of their ease of incorporation and ready means of detection. Substitution with positron-emitting isotopes, such as $^{11}C$, $^{18}F$, $^{15}O$ and $^{13}N$, can be useful in positron emission tomography (PET) studies for examining substrate receptor occupancy. Isotopically labeled compounds of the present invention can generally be prepared by processes analogous to those described in the accompanying Schemes and/or in the Examples and Preparations, by using an appropriate isotopically labeled reagent in place of the non-labeled reagent previously employed. Pharmaceutically acceptable solvates in accordance with the invention include those wherein the solvent of crystallization may be isotopically substituted, e.g., $D_2O$, acetone-$d_6$, or DMSO-$d_6$.

The term "stereoisomer" refers to isomers with at least one asymmetric center. A compound having one or more (e.g., one, two, three or four) asymmetric centers can give rise to a racemic mixture, single enantiomer, diastereomer mixture and individual diastereomer. Certain individual molecules may exist as geometric isomers (cis/trans). Similarly, the compound of the present invention may exist as a mixture of two or more structurally different forms in rapid equilibrium (generally referred to as tautomer). Typical examples of a tautomer include a keto-enol tautomer, phenol-keto tautomer, nitroso-oxime tautomer, imine-enamine tautomer and the like. It is to be understood that all such isomers and mixtures thereof in any proportion (such as 60%, 65%, 70%, 75%, 80%, 85%, 90%, 95%, 96%, 97%, 98%, and 99%) are encompassed within the scope of the present invention.

The chemical bonds of the compound of the present invention may be depicted herein using a solid line (), a solid wedge (), or a dotted wedge (). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Unless stated otherwise, it is intended that the compound of the present invention can exist as stereoisomers, which include cis and trans isomers, optical isomers such as R and S enantiomers, diastereomers, geometric isomers, rotational isomers, conformational isomers, atropisomers, and mixtures thereof. The compound of the present invention may exhibit more than one type of isomerism, and consist of mixtures thereof (such as racemates and diastereomeric pairs).

The present invention includes all possible crystalline forms or polymorphs of the compound of the present invention, either as a single polymorph, or as a mixture of more than one polymorphs, in any ratio.

It also should be understood that, certain compounds of the present invention can be used for the treatment in a free form, or where appropriate, in a form of a pharmaceutically acceptable derivative. In the present invention, the pharmaceutically acceptable derivative includes, but is not limited to a pharmaceutically acceptable salt, ester, solvate, N-oxide, metabolite or prodrug, which can directly or indirectly provide the compound of the present invention or a metabolite or residue thereof after being administered to a patient in need thereof. Therefore, "the compound of the present invention" mentioned herein also means to encompass various derivative forms of the compound as mentioned above.

A pharmaceutically acceptable salt of the compound of the present invention includes an acid addition salt and a base addition salt thereof.

A suitable acid addition salt is formed from an acid which forms a pharmaceutically acceptable salt. Specific examples include acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

A suitable base addition salt is formed from a base which forms a pharmaceutically acceptable salt. Specific examples include aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, 2002). The method for preparing a pharmaceutically acceptable salt of the compound of the present invention is known to a person skilled in the art.

As used herein, the term "ester" refers to those derived from the compounds of the various formulae in the present application, which include physiologically-hydrolyzable esters (which may be hydrolyzed under physiological conditions to release the compounds of the present invention in the form of free acids or alcohols). The compound of the present invention itself may be an ester as well.

The compound of the present invention can exist as a solvate (preferably a hydrate), wherein the compound of the present invention contains a polar solvent, in particular water, methanol or ethanol for example, as a structural element of the crystal lattice of the compound. The amount of the polar solvent, in particular water, may exist in a stoichiometric or non-stoichiometric ratio.

As can be appreciated by a person skilled in the art, not all nitrogen containing heterocycles can form N-oxides since the nitrogen requires an available lone-pair electron for oxidation to the oxide; a person skilled in the art will recognize those nitrogen containing heterocycles which can form N-oxides. A person skilled in the art will also recognize that tertiary amines can form N-oxides. Synthetic methods for the preparation of N-oxides of heterocycles and tertiary amines are well known to a person skilled in the art, and they include the oxidation of heterocycles and tertiary amines with peroxy acids such as peracetic acid and m-chloroperbenzoic acid (MCPBA), hydrogen peroxide, alkyl hydroperoxides such as tert-butyl hydroperoxide, sodium perborate, and dioxiranes such as dimethyldioxirane. These methods for the preparation of N-oxides have been extensively described and reviewed in literatures, see e.g., T. L. Gilchrist, *Comprehensive Organic Synthesis*, vol. 7, pp 748-750; A. R. Katritzky and A. J. Boulton, Eds., Academic Press; and G. W. H. Cheeseman and E. S. G. Werstiuk, *Advances in Heterocyclic Chemistry*, vol. 22, pp 390-392, A. R. Katritzky and A. J. Boulton, Eds., Academic Press.

The metabolite of the compound of the present invention, namely a substance formed in vivo upon administration of the compound of the present invention, is also included within the scope of the present invention. Such a product may result e.g., from the oxidation, reduction, hydrolysis, amidation, de-amidation, esterification, enzymolysis, and the like, of the administered compound. Accordingly, the present invention encompasses the metabolite of the compound of the present invention, including a compound produced by a method comprising contacting the compound of the present invention with a mammal for a period of time sufficient to result in a metabolic product thereof.

Also within the scope of the present invention is a prodrug of the compound of the invention, which is certain derivative of the compound of the invention that may have little or no pharmacological activity itself, but can, when administered into or onto the body, be converted into the compound of the invention having the desired activity, for example, by hydrolytic cleavage. In general, such prodrug will be a functional derivative of the compound which is readily converted in vivo into the compound with desired therapeutic activity. Further information on the use of the prodrug may be found in "Pro-drugs as Novel Delivery Systems", Vol. 14, ACS Symposium Series (T. Higuchi and V. Stella). The prodrug in accordance with the invention can, for example, be produced by replacing appropriate functionalities present in the compound of the present invention with certain moieties known to those skilled in the art as "pro-moieties" as described, for example, in "Design of Prodrugs" by H. Bundgaard (Elsevier, 1985).

The present invention further encompasses the compound of the present invention having a protecting group. During any of the processes for preparation of the compound of the present invention, it may be necessary and/or desirable to protect sensitive or reactive groups on any of the molecules concerned, thereby resulting in the chemically protected form of the compound of the present invention. This may be achieved by means of conventional protecting groups, e.g., those described in T. W. Greene & P. G. M. Wuts, Protective Groups in Organic Synthesis, John Wiley & Sons, 1991, which is incorporated herein by reference. The protecting groups may be removed at a convenient subsequent stage using methods known from the art.

The term "about" refers to a range within ±10%, preferably within ±5%, and more preferably within ±2% of the specified value.

The term "effective amount" refers to an amount sufficient to achieve the desired therapeutic effect, under the conditions of administration, and it causes an improvement in the pathological symptoms, disease progression, physiological conditions associated with or induces resistance to succumbing to the afore mentioned disorders.

Unless otherwise indicated, the term "treat", "treating" or "treatment", as used herein, means reversing, alleviating, inhibiting the progress of, or preventing the disorder or condition to which such term applies, or one or more symptoms of such disorder or condition.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g., birds, amphibians, reptiles) and mammals, such as non-human primates, livestock and/or domesticated animals (such as sheep, dog, cat, cow, pig and the like).

MODE OF CARRYING OUT THE INVENTION

In some embodiments, the present disclosure provides a method for preventing, alleviating and/or treating idiopathic pulmonary fibrosis, comprising administering to a subject in need thereof an effective amount of a compound of Formula (I) or a pharmaceutically acceptable salt, ester, stereoisomer, polymorph, solvate, N-oxide, isotopically labeled compound, metabolite or prodrug thereof:

(I)

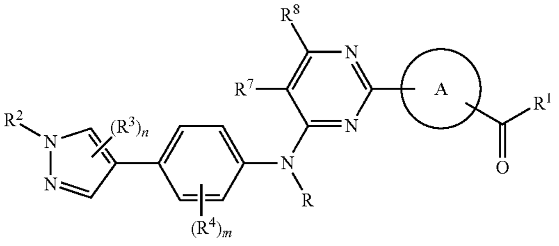

wherein:

ring A is

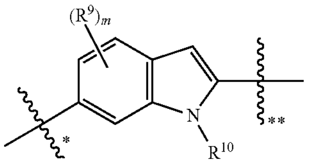

or

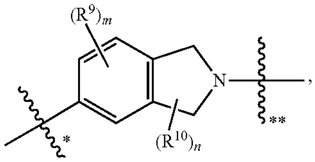

, the above group is attached to the pyrimidine ring at either of the two positions labeled * or **, and is attached to the carbonyl group at the other position;

R is selected from the group consisting of H and $C_{1-6}$ alkyl;

$R^1$ is

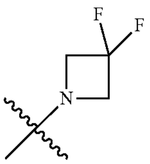

or

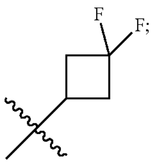

;

$R^2$ is selected from the group consisting of H and $C_{1-6}$ alkyl;

$R^3$, $R^4$, $R^7$ and $R^8$, at each occurrence, are each independently selected from the group consisting of H, halogen, —$NR^5R^6$, —OH, $C_{1-6}$ alkyl and —$OR^5$;

$R^9$ and $R^{10}$, at each occurrence, are each independently selected from the group consisting of H, halogen, $C_{1-6}$ alkyl, $C_{2-6}$ alkenyl, $C_{3-10}$ cyclic hydrocarbyl, 3-10-membered heterocyclyl, $C_{6-10}$ aryl, 5-14-membered heteroaryl, $C_{6-12}$ aralkyl, —C(═O)$R^5$ and —$C_{1-6}$ alkylene-O(P═O)$(OH)_2$;

the above alkylene, alkyl, alkenyl, cyclic hydrocarbyl, heterocyclyl, aryl, heteroaryl and aralkyl, at each occurrence, are each optionally substituted with one or more substituents independently selected from the group consisting of halogen, $C_{1-6}$ alkyl and —$OR^5$;

$R^5$ and $R^6$, at each occurrence, are each independently selected from the group consisting of H, $C_{1-6}$ alkyl, $C_{3-10}$ cyclic hydrocarbyl, 3-10-membered heterocyclyl, $C_{6-10}$ aryl, 5-14-membered heteroaryl and $C_{6-12}$ aralkyl;

m, at each occurrence, is each independently an integer of 0, 1, 2 or 3; and n, at each occurrence, is each independently an integer of 0, 1 or 2.

In preferred embodiments, ring A is

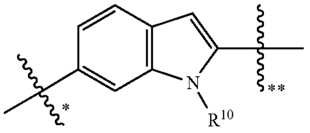

or

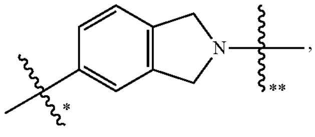

, the above group is attached to the pyrimidine ring at the position labeled *, and is attached to the carbonyl group at the position labeled **, wherein $R^{10}$ is selected from the group consisting of H and $C_{1-6}$ alkyl, preferably is H or methyl.

In preferred embodiments, ring A preferably is

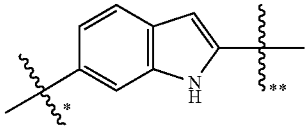,

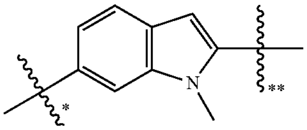 or

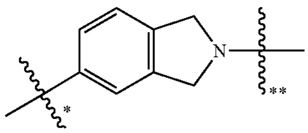, the above group is attached to the pyrimidine ring at the position labeled *, and is attached to the carbonyl group at the position labeled **.

In preferred embodiments, R is H.

In preferred embodiments, $R^2$ is H.

In preferred embodiments, $R^5$ and $R^6$, at each occurrence, are each independently selected from the group consisting of H, methyl and ethyl.

In preferred embodiments, $R^3$, $R^4$, $R^7$ and $R^8$, at each occurrence, are each independently selected from the group consisting of H, F, Cl, Br, I, —$NH_2$, —OH, methyl, trifluoromethyl, —$CH_2$-Ph, methoxy, ethoxy and —$CH_2OCH_3$.

In preferred embodiments, $R^3$ is H.

In preferred embodiments, $R^4$ is selected from the group consisting of H and halogen (e.g., F, Cl, Br or I), preferably is H or F.

In preferred embodiments, $R^7$ is selected from the group consisting of H and halogen (e.g., F, Cl, Br or I), preferably is H or F.

In preferred embodiments, $R^8$ is H.

In preferred embodiments, $R^9$ and $R^{10}$, at each occurrence, are each independently selected from the group consisting of H, F, Cl, Br, methyl, ethyl, n-propyl, isopropyl, vinyl, cyclopropyl, cyclobutyl, cyclopentyl, oxetanyl, monofluoromethyl, difluoromethyl, trifluoromethyl, acetyl, —$CH_2CHF_2$, —$CH_2OH$, —$CH_2OCH_3$, —$CH_2CH_2OCH_3$, —$CH_2$—O(P═O)$(OH)_2$,

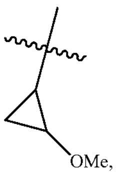, 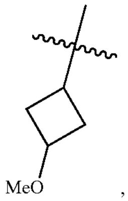, 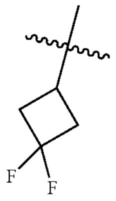 and 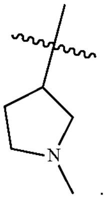.

In preferred embodiments, $R^9$, at each occurrence, is each independently selected from the group consisting of H, $C_{1-6}$ alkyl, $C_{3-10}$ cyclic hydrocarbyl, 3-10-membered heterocyclyl, $C_{6-10}$ aryl, 5-14-membered heteroaryl and $C_{6-12}$ aralkyl, preferably is H.

In preferred embodiments, $R^{10}$, at each occurrence, is each independently selected from the group consisting of H and $C_{1-6}$ alkyl, preferably is H, methyl, ethyl, n-propyl or isopropyl, and most preferably is H or methyl.

In preferred embodiments, the present disclosure provides a method for preventing, alleviating and/or treating idiopathic pulmonary fibrosis, comprising administering to a subject in need thereof an effective amount of a compound of Formula (II) or a pharmaceutically acceptable salt, ester, stereoisomer, polymorph, solvate, N-oxide, isotopically labeled compound, metabolite or prodrug thereof:

(II)

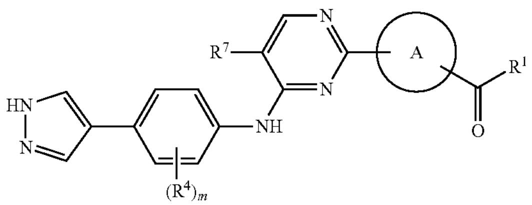

wherein each of the groups is as defined above.

In preferred embodiments, the present disclosure provides a method for preventing, alleviating and/or treating idiopathic pulmonary fibrosis, comprising administering to a subject in need thereof an effective amount of a compound of Formula (III) or a pharmaceutically acceptable salt, ester, stereoisomer, polymorph, solvate, N-oxide, isotopically labeled compound, metabolite or prodrug thereof:

(III)

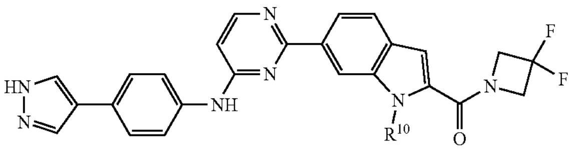

wherein $R^{10}$ is H or methyl, preferably is methyl.

In preferred embodiments, the compound has the following structure:

| Compound No. | Structure |
|---|---|
| 006 | 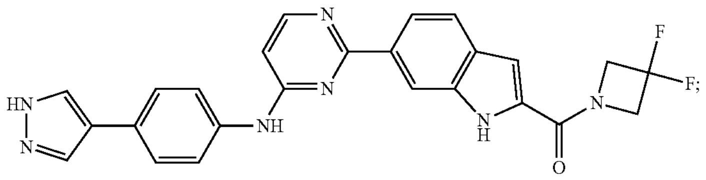 [SMILES: O=C(c1cc2ccc(-c3nccc(Nc4ccc(-c5cn[nH]c5)cc4)n3)cc2[nH]1)N1CC(F)(F)C1] |
| 007 | 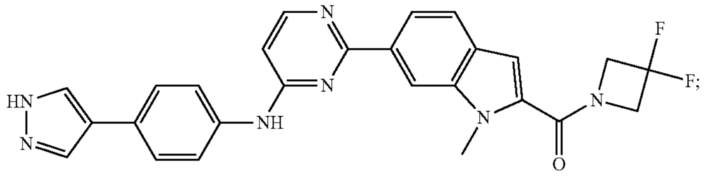 [SMILES: Cn1c(C(=O)N2CC(F)(F)C2)cc2ccc(-c3nccc(Nc4ccc(-c5cn[nH]c5)cc4)n3)cc21] |
| 008 | 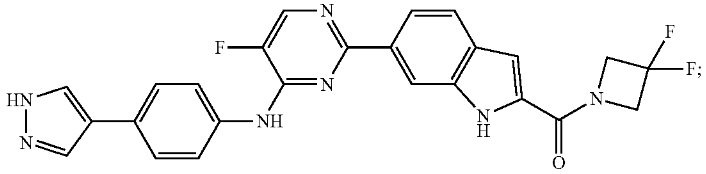 [SMILES: O=C(c1cc2ccc(-c3ncc(F)c(Nc4ccc(-c5cn[nH]c5)cc4)n3)cc2[nH]1)N1CC(F)(F)C1] |
| 009 | 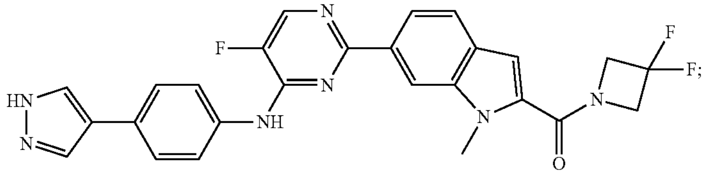 [SMILES: Cn1c(C(=O)N2CC(F)(F)C2)cc2ccc(-c3ncc(F)c(Nc4ccc(-c5cn[nH]c5)cc4)n3)cc21] |
| 010 | 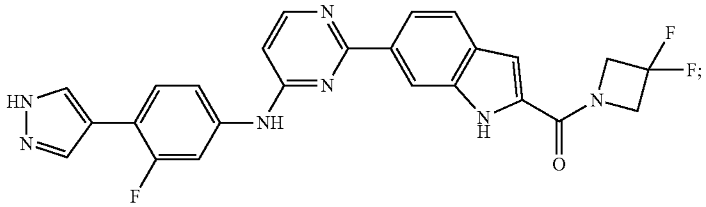 |
| 011 | 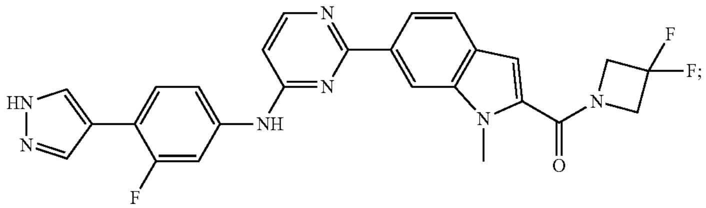 [SMILES: O=C(c1cc2ccc(-c3nccc(Nc4ccc(-c5cn[nH]c5)c(F)c4)n3)cc2[nH]1)N1CC(F)(F)C1] |
| 020 | 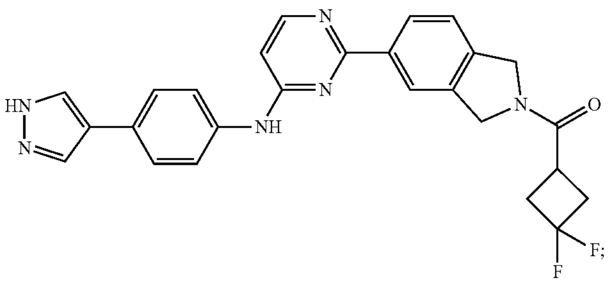 [SMILES: O=C(C1CC(F)(F)C1)N1Cc2ccc(-c3nccc(Nc4ccc(-c5cn[nH]c5)cc4)n3)cc2C1] |

-continued

| Compound No. | Structure |
|---|---|
| 021 | 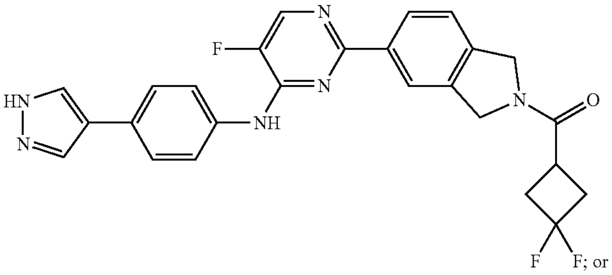 F; or |
| 022 | 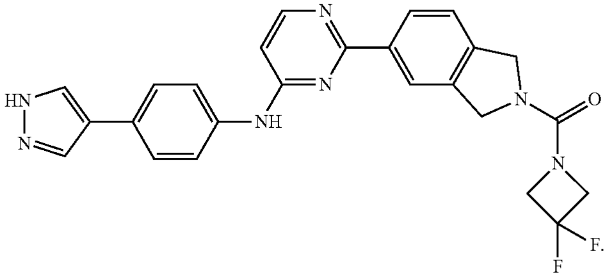 |

In some embodiments, the compounds are prepared according to the methods disclosed in WO 2019/001572 A1 (incorporated herein by reference).

In some embodiments, the compound of Formula (I), (II) or (III) or a pharmaceutically acceptable salt, ester, stereoisomer, polymorph, solvate, N-oxide, isotopically labeled compound, metabolite or prodrug thereof is administered in an amount of about 0.005 mg/day to about 5000 mg/day, e.g., in an amount of about 0.005, 0.05, 0.5, 5, 10, 20, 30, 40, 50, 100, 150, 200, 250, 300, 350, 400, 450, 500, 550, 600, 650, 700, 750, 800, 850, 900, 950, 1000, 1500, 2000, 2500, 3000, 3500, 4000, 4500 or 5000 mg/day.

In some embodiments, the compound of Formula (I), (II) or (III) or a pharmaceutically acceptable salt, ester, stereoisomer, polymorph, solvate, N-oxide, isotopically labeled compound, metabolite or prodrug thereof is administered in an amount of about 1 ng/kg to about 200 mg/kg, about 1 pg/kg to about 100 mg/kg or about 1 mg/kg to about 50 mg/kg body weight per day, e.g., is administered in an amount of about 1 μg/kg, about 10 μg/kg, about 25 μg/kg, about 50 μg/kg, about 75 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg/kg, about 350 μg/kg, about 375 μg/kg, about 400 μg/kg, about 425 μg/kg, about 450 μg/kg, about 475 μg/kg, about 500 μg/kg, about 525 μg/kg, about 550 μg/kg, about 575 μg/kg, about 600 μg/kg, about 625 μg/kg, about 650 μg/kg, about 675 μg/kg, about 700 μg/kg, about 725 μg/kg, about 750 μg/kg, about 775 μg/kg, about 800 μg/kg, about 825 μg/kg, about 850 μg/kg, about 875 μg/kg, about 900 μg/kg, about 925 μg/kg, about 950 μg/kg, about 975 μg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg or about 300 mg/kg body weight per unit dose.

In some embodiments, the daily dose of the compound of Formula (I), (II) or (III) or a pharmaceutically acceptable salt, ester, stereoisomer, polymorph, solvate, N-oxide, isotopically labeled compound, metabolite or prodrug thereof is administered at one time or is administered in two, three or four doses.

In some embodiments, the compound of Formula (I), (II) or (III) or a pharmaceutically acceptable salt, ester, stereoisomer, polymorph, solvate, N-oxide, isotopically labeled compound, metabolite or prodrug thereof is administered continuously for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 1 month, at least 2 months, at least 3 months, at least 4 months, at least 5 months, at least 6 months, at least 1 year, or at least 2 years.

In some embodiments, the compound of Formula (I), (II) or (III) or a pharmaceutically acceptable salt, ester, stereoisomer, polymorph, solvate, N-oxide, isotopically labeled compound, metabolite or prodrug thereof is administered for one or more (e.g., 1, 2, 3, 4, 5, 6, 7, 8, 9 or 10) courses of treatment, wherein each course of treatment lasts for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days or at least 50 days; and the interval between every two courses of treatment is 0, 1, 2, 3, 4, 5, 6, 7, 8, 9, 10 days, two weeks, three weeks, or four weeks.

In some embodiments, the compound of Formula (I), (II) or (III) or a pharmaceutically acceptable salt, ester, stereoisomer, polymorph, solvate, N-oxide, isotopically labeled compound, metabolite or prodrug thereof is administered in compound, metabolite or prodrug thereof is administered through injection (e.g., intravenous, intraarterial, subcutaneous, intraperitoneal, intramuscular injection, including dripping), or transdermal administration, or is administered via oral, buccal, nasal, transmucosal, topical, as an ophthalmic formulation, or via inhalation.

In some embodiments, the compound of Formula (I), (II) or (III) or a pharmaceutically acceptable salt, ester, stereoisomer, polymorph, solvate, N-oxide, isotopically labeled compound, metabolite or prodrug thereof is administered in a dosage form selected from the group consisting of tablet, capsule, lozenge, hard candy, powder, spray, cream, salve, suppository, gel, paste, lotion, ointment, aqueous suspensions, injectable solution, elixir, and syrup.

The present disclosure encompasses any combination of the above embodiments.

EXAMPLE

In order to make the objects and technical solutions of the invention clearer, the invention will be further described below with reference to specific examples. It should be understood that the following examples are only intended for illustrating the invention and are not to be understood as limiting the scope of the invention. Further, specific experimental methods not mentioned in the following examples are carried out in accordance with conventional experimental methods.

Compound 128 employed in the examples has the following structure, and was prepared according to the method disclosed in WO 2019/001572 A1.

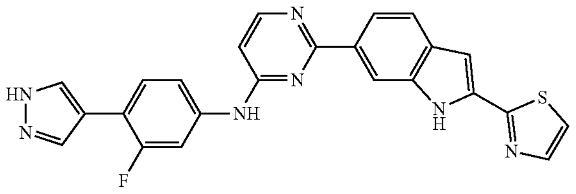 [SMILES: Fc1cc(Nc2ccnc(-c3ccc4cc(-c5nccs5)[nH]c4c3)n2)ccc1-c1cn[nH]c1]

Example 1. ROCK2 Kinase Activity Assay

The kinase $IC_{50}$ was determined by a commercialized CISBIO kinase detection kit, HTRF KinEASE-STK S2 kit (62ST2PEC). ROCK2 (01-119) employed in the reaction was purchased from Carna Biosciences.

Before the assay, the following working solutions as needed were formulated with corresponding reagents according to the instruction of the kinase detection kit: 1×kinase buffer, 5×STK-S2 substrate working solution (1.5 μM) and 5×ATP working solution (1.5 μM), 5×ROCK2 kinase working solution, 4×Streptavidin-XL665 working solution, and 4×STK-Ab-Cryptate 2 detection solution. Then the assay was performed according to the following procedure.

A solution of a compound at a concentration of 10000 nM was prepared with the 1×kinase buffer containing 2.5% DMSO. Gradient dilution of the solution of the compound was performed with the kinase buffer containing DMSO, so as to obtain solutions of a test compound at 9 different concentrations. In addition to wells of test compounds, a positive well (containing all the reagents except the compound) and a negative well (containing all the reagents except the test compound and kinase) were set. Except for the control wells (positive and negative wells), a solution of a test compound (4 μL) was added to each of the reaction wells, and a solution of 2.5% DMSO was added to the control wells. Then the substrate (2 μM, i.e., 2 μL 5×STK-S2 substrate working solution) was added to each of the reaction wells. The 5×ROCK2 kinase working solution (2 μL, containing 1.4 ng ROCK2 kinase) was added to each of the reaction wells except for the negative well, the volume of which was made up with the 1×kinase buffer (2 μL). The 5×ATP working solution (2 μL) was added to each of the reaction wells, and the mixtures were incubated at room temperature for 2 hours. After the kinase reaction was complete, the 4×Streptavidin-XL665 working solution was added to each of the reaction wells, the solutions were mixed, followed by immediate addition of the 4×STK-Ab-Cryptate 2 detection solution (5 μL), and the mixtures were incubated at room temperature for 1 hour. The fluorescence signal was read on ENVISION (Perkinelmer) (excitation wavelength: 320 nm, and emission wavelength: 665 nm and 615 nm). The inhibitory rate in each well was calculated based on the fluorescence intensity value: ER (Emission Ratio)=(fluorescence intensity at 665 nm/fluorescence intensity at 615 nm); inhibitory rate=$(ER_{positive}-ER_{test\ compound})/(ER_{positive}-ER_{negative})*100\%$. Curves were plotted and fitted to obtain the median inhibitory concentration ($IC_{50}$) of each teat compound with the PRISM 5.0 software. The $IC_{50}$ values of the compounds are as shown in the following table.

TABLE 1

| Compound | ROCK2 $IC_{50}$ nM |
|---|---|
| Compound 006 | 34 |
| Compound 007 | 33 |
| Compound 008 | 24 |
| Compound 009 | 12 |
| Compound 010 | 61 |
| Compound 011 | 9 |
| Compound 020 | 44 |
| Compound 021 | 45 |
| Compound 022 | 75 |
| Compound 128 | 27 |

Example 2. Therapeutic Effect on Idiopathic Pulmonary Fibrosis (IPF) of Compounds Detected in BLM-Induced Mouse IPF Model 60 C57BL/6 mice (purchased from SLAC, Shanghai) were adaptively fed for 1 week, and 50 animals were randomly selected. 3 mg/kg of bleomycin (BLM, purchased from SIGMA, #SIGMA-P9564) was administered through intratracheal (IT) injection to the mice to establish the IPF animal model. The remaining 10 animals were injected with physiological saline at a volume same as the injected BLM, and served as the normal group (N=10). The day of the injection of bleomycin was set as day 0 (DO); on day 6, the animals were randomly divided into 4 groups according to body weight: vehicle group (N=14), compound 007 administration group (N=12), compound 128 administration group (N=12), and positive control pirfenidone (purchased from SIGMA, #SIGMA-P2116) administration group (N=12). The animal groups are shown in Table 2.

TABLE 2

| Animal grouping | | | | | |
|---|---|---|---|---|---|
| NO. | Group | Administration | Animal number | Dose and administration frequency | Administration route and time |
| 1 | Normal group | vehicle 1 | 10 | 10 ml/kg body weight, once a day | orally administered, for 14 consecutive days |
| 2 | Vehicle group | vehicle 1 | 14 | 10 ml/kg body weight, once a day | orally administered, for 14 consecutive days |
| 3 | Compound 007 administration group | compound 007 | 12 | 100 mg/kg body weight, once a day | orally administered, for 14 consecutive days |
| 4 | Compound 128 administration group | compound 128 | 12 | 100 mg/kg body weight, once a day | orally administered, for 14 consecutive days |
| 5 | Pirfenidone administration group | pirfenidone | 12 | 90 mg/kg body weight, twice a day | orally administered, for 14 consecutive days |

The animals in each group were administered on days 8-21: the animals in the normal group and vehicle group were intragastrically administered with vehicle 1 (vehicle 1: 20% PEG 400+5% Tween 80+75% $ddH_2O$), the animals in the compound 007 administration group were intragastrically administered with compound 007 (formulated with vehicle 1), the animals in the compound 128 administration group were intragastrically administered with compound 128 (formulated with vehicle 1), and the animals in the Pirfenidone administration group were intragastrically administered with pirfenidone (vehicle 2: 0.2% Methyl cellulose+0.5% Tween 80+99.3% $ddH_2O$).

Figure 1B:
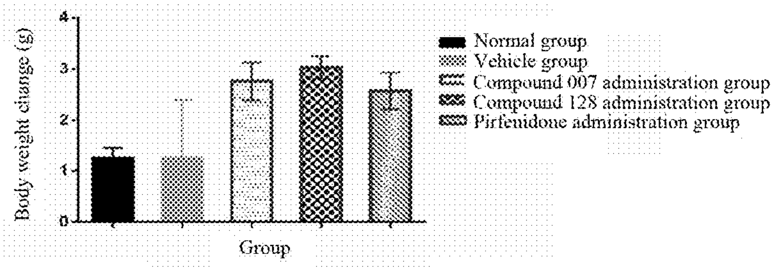
FIG. 1B shows the body weight change of the animals in each group at the end of the test in Example 2.

The body weight and its changes were recorded daily (the calculation formula for the body weight change on day 21: Body weight change on day 21=Body weight on day 21—Body weight on day 0), and the results are shown in FIGS. 1A and 1B.

Figure 2:
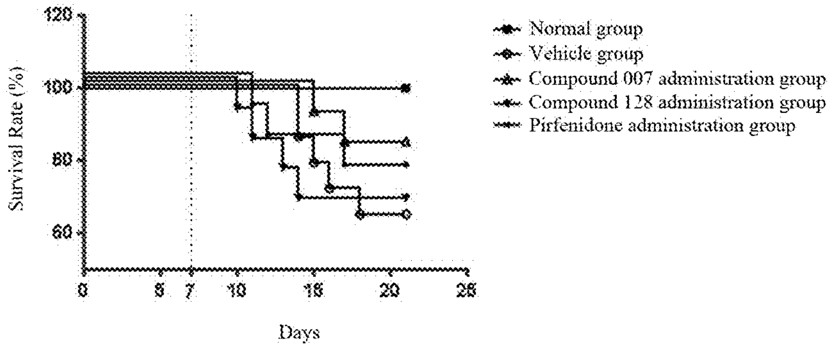
FIG. 2 shows the survival rate of the animals in each group during the test in Example 2.

The survival rate of the animals was recorded, and results are shown in FIG. 2. According to the results in FIG. 2, at the end of the test, the survival rate of the animals in the compound 007 administration group was significantly higher, indicating that compound 007 is better tolerated.

Figure 3:
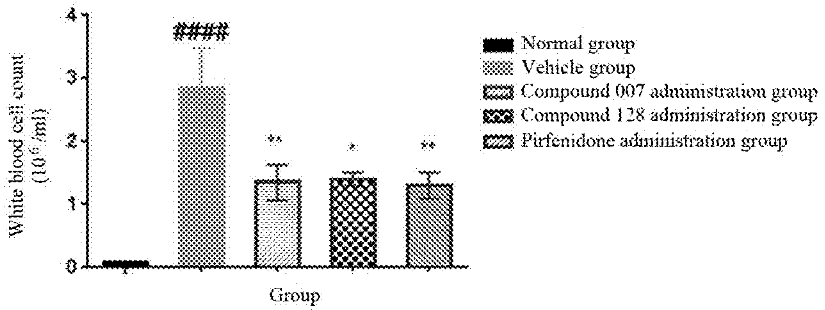
FIG. 3 shows the white blood cell count in the alveolar lavage fluid of the animals in each group after the administration in Example 2.

The animals were euthanized 2 hours after the administration on day 21, and the alveolar lavage fluid was collected for white blood cell (WBC) counting. Results are shown in FIG. 3. According to FIG. 3, there was no significant difference in the total white blood cell count in the alveolar lavage fluid of the animals in each administration group.

Figure 4A:
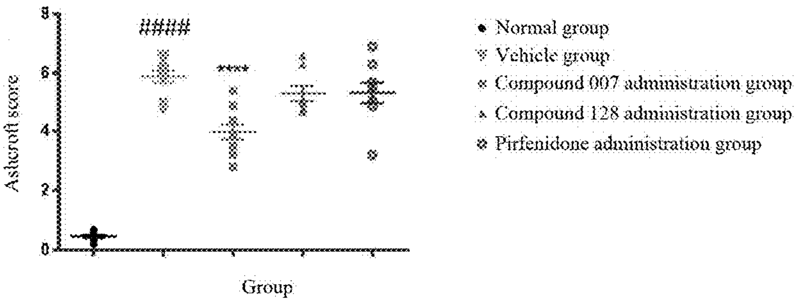
FIG. 4A shows the lung tissue fibrosis score of the animals in each group after the administration in Example 2.
Figure 4B:
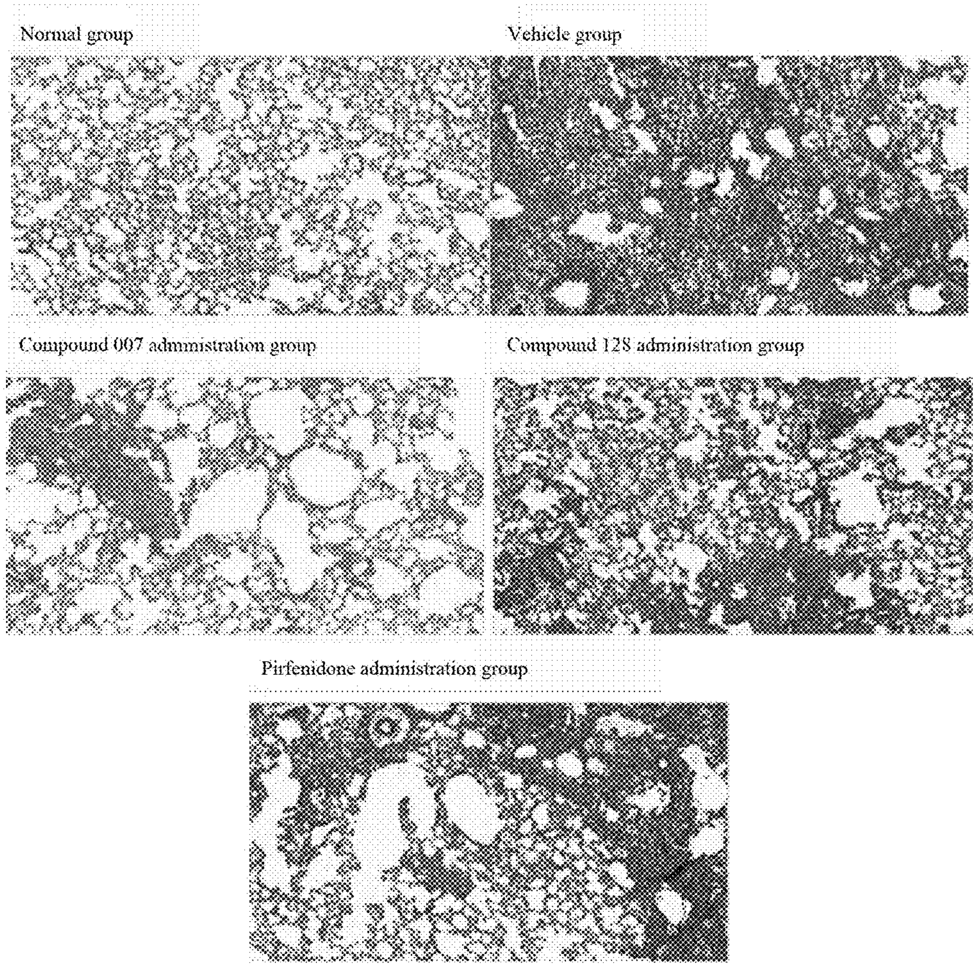
FIG. 4B shows the representative Masson Trichome staining pathological photos of each group in Example 2.

The left lung of the animals was fixed for histopathological examination, and the Ashcroft score of lung injury was performed by Masson Trichome staining. The scoring standard is as reported in Ashcroft T et al., Journal of clinical pathology, 1988. After 100 times magnification, each successive field was scored (ranging from 0 (normal lung)) to 8 (total fibrous obliteration within the field). The mean score of 5 fields was taken, and the results are shown in FIGS. 4A and 4B. According to the results in FIGS. 4A and 4B, after the administration, compound 007 significantly reduced the collagen accumulation in lung and the degree of lung fibrosis in the mice. The therapeutic effect was significantly better than that of pirfenidone and compound 128.

The mRNA levels of lung tissue fibrosis-associated protein collagen 1A1 (COL1A1) and tissue inhibitor of metal matrix protein 1 (TIMP-1) in the lung tissue after the administration was detected by a real-time fluorescent quantitative PCR method. Specifically, the lung tissue fragments were transferred to a centrifuge tube containing 1 mL of TRIzol reagent (Invitrogen, catalog No. 15596018). The lung tissue was ground at low temperature by a tissue grinder. Total RNA in cells was extracted. TransScript All-in-One First-Strand cDNA Synthesis SuperMix for qPCR (One-Step gDNA Removal) (TransGen, catalog No. AT341-02) kit was used for reverse transcription synthesis of cDNA. The mRNA expression changes of COL1A1 and TIMP-1 in the lung tissue was detected by a fluorescence quantitative PCR method.

In the real-time fluorescent quantitative PCR method, β-actin gene was used as the internal reference gene to normalize the data. All primer sequences were from the PrimerBank website, ID No.: 34328108a1 (COL1A1 primer), 6755795a1 (TIMP-1 primer) and 6671509a1 (β-actin primer). All of the 3 primers were synthesized by Invitrogen.

Figure 5A:
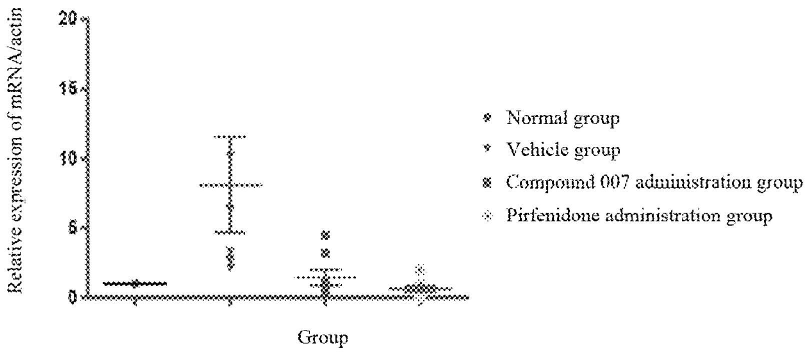
FIG. 5A shows the expression of TIMP-1 mRNA in lung tissues of the animals in each group after the administration in Example 2.
Figure 5B:
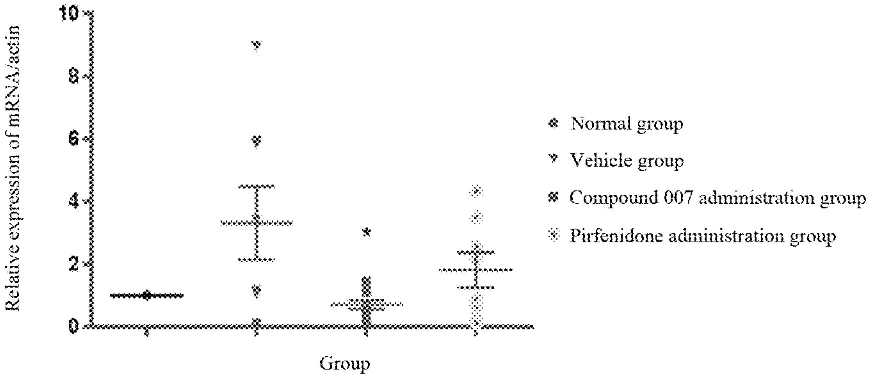
FIG. 5B shows the expression of COL1A1 mRNA in the lung tissue of the animals in each group after the administration in Example 2.

The results are shown in FIGS. 5A and 5B. According to the results, the up-regulation of TIMP-1 expression in the lung tissue induced by bleomycin was significantly inhibited by compound 007 ($P<0.05$). Pirfenidone achieved a moderate inhibitory effect without statistic difference. The up-regulation of COL1A1 expression induced by bleomycin was significantly inhibited by compound 007 and pirfenidone.

Example 3. Therapeutic Effect on Idiopathic Pulmonary Fibrosis (IPF) of Compounds at Different Doses Detected in BLM-Induced Mouse IPF Model After adaptive feeding, C57BL/6J mice were randomly divided into 2 groups according to body weight: in one group, 15 animals were administered with 50 μL physiological saline through intratracheal injection; and in another group, 90 animals were administered with 50 μL bleomycin (2.5 mg/kg) through intratracheal injection to establish the IPF model. On Day 7 after the establishment of the animal model, animals were randomly grouped according to the weight change (the difference between the weight on Day 7 after the establishment of the model and the day when the model was established). Drugs were administered for 14 consecutive days from the eighth day after the establishment of the animal model. The animal groups and administration information are shown in Table 3.

TABLE 3

| Animal grouping and dosage regimen | | | | | |
|---|---|---|---|---|---|
| Group | Animal numbers | Model establishment (tracheal/once 50 μL) | drug/route/frequency | Administration Volume (ml/kg) | Administration Time (day) |
| Normal group | 15 | physiological saline | 0.5% CMC-Na; orally administered; once a day | 10 | 14 |
| Model group | 15 | Bleomycin 2.5 mg/kg | 0.5% CMC-Na; orally administered; once a day | 10 | 14 |
| Pirfenidone - 90 mpk | 15 | Bleomycin 2.5 mg/kg | Pirfenidone 90 mg/kg; orally administered; twice a day | 10 | 14 |
| Nintedanib - 30 mpk | 15 | Bleomycin 2.5 mg/kg | Nintedanib 30 mg/kg; orally administered; once a day | 10 | 14 |
| Compound 007 - 30 mpk | 15 | Bleomycin 2.5 mg/kg | Compound 007 30 mg/kg; orally administered; once a day | 10 | 14 |
| Compound 007 - 100 mpk | 15 | Bleomycin 2.5 mg/kg | Compound 007 100 mg/kg; orally administered; once a day | 10 | 14 |
| Compound 007 - 300 mpk | 15 | Bleomycin 2.5 mg/kg | Compound 007 300 mg/kg; orally administered; once a day | 10 | 14 |

Figure 6:
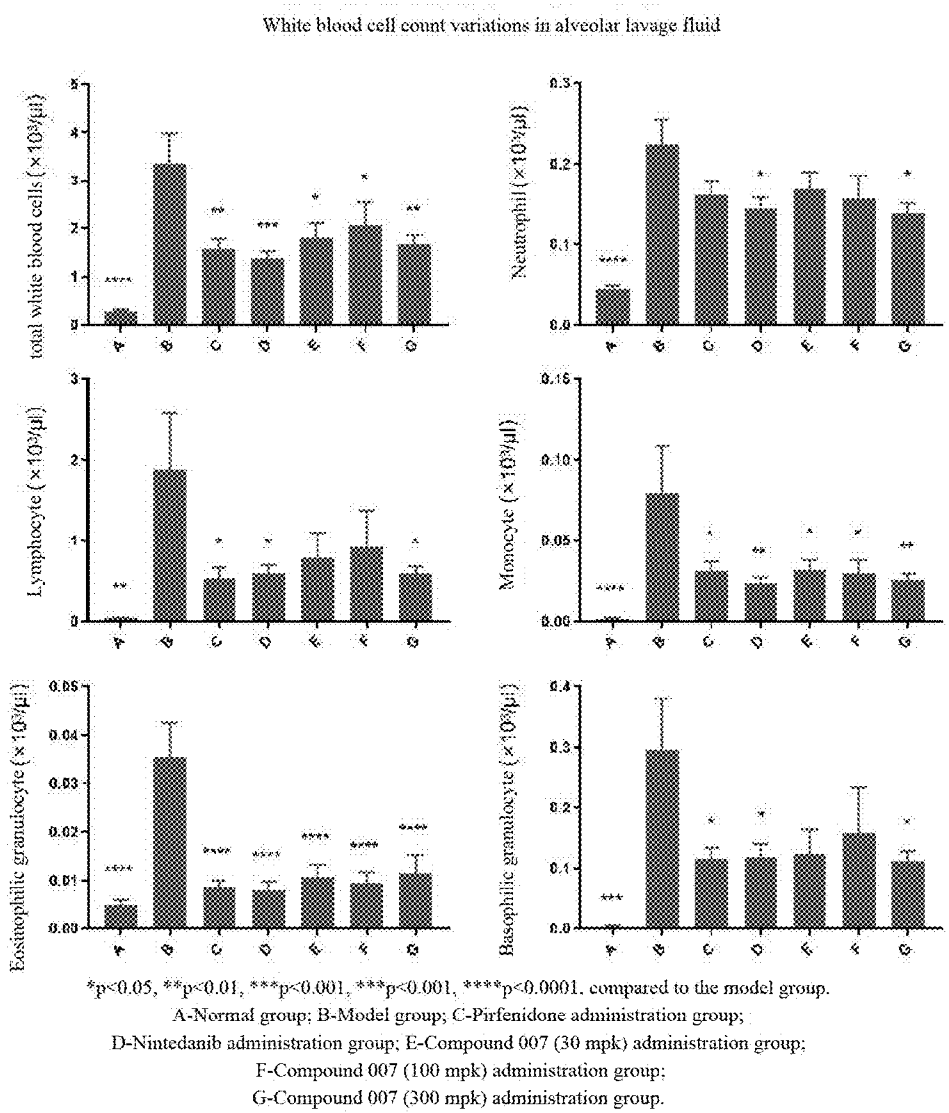
FIG. 6 shows the white blood cell count in the alveolar lavage fluid of the animals in each group after the administration in Example 3.

Animals were sacrificed by bleeding from the inferior vena cava 2 hours after the last administration. The bronchoalveolar lavage fluid (BALF) was collected for white blood cell count. The results are shown in FIG. 6.

The left lung of the animals was fixed for preparing histopathological slide. H&E and Masson Trichome staining were performed to score the degree of lung injury and fibrosis. Pulmonary fibrosis scoring standard was according to "Standardized quantification of pulmonary fibrosis in histological samples"; lung tissue injury grade score is 0-16, mainly evaluated from four aspects including inflammatory cell infiltration (0-4), hemorrhage (0-4), interstitial and alveolar edema (0-4) and alveolar septum thickness (0-4). A higher score indicate a higher degree of lung tissue injury.

Figure 7A:
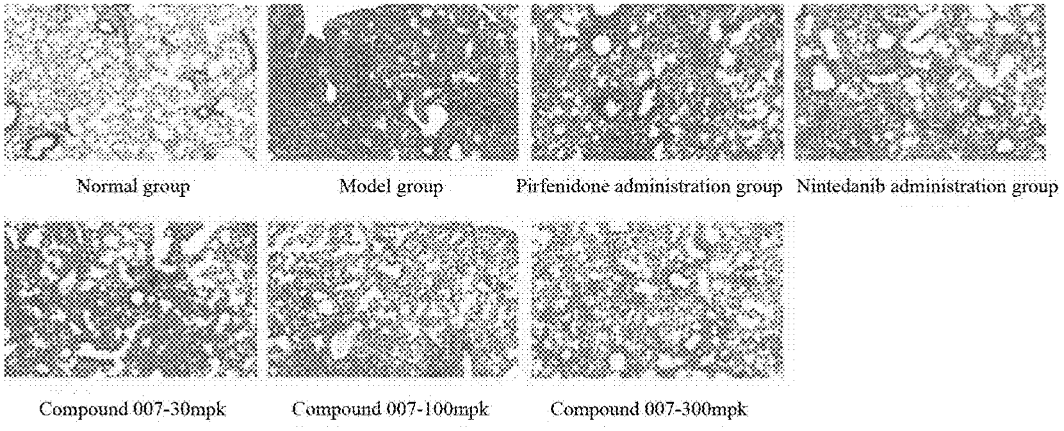
FIG. 7A shows representative H&E staining pathological staining photos of each group in Example 3.

Compared with the model group, compound 007 can significantly reduce the infiltration of white blood cells in the lung (FIG. 6), and the lung injury (FIGS. 7A and 7B) and the fibrosis degree (FIGS. 8A and 8B) were also significantly improved. Among them, the therapeutic effects of compound 007-30 mpk and 100 mpk were equivalent to those of pirfenidone and nintedanib. Compound 007-300 mpk was superior to pirfenidone and nintedanib in respect of lung injury and fibrosis degree improvements. It indicates that compound 007 achieves its therapeutic effect on IPF by reducing the infiltration of white blood cells in lung, improving lung injury and pulmonary fibrosis, etc.

Various modifications to the invention in addition to those described herein will become apparent to those skilled in the art from the foregoing description. Such modifications are intended to fall within the scope of the appended claims. Each reference, including all patents, applications, journal articles, books and any other disclosure, referred to herein is hereby incorporated by reference in its entirety.

What is claimed is:

1. A method for preventing, alleviating and/or treating idiopathic pulmonary fibrosis, comprising administering to a subject in need thereof an effective amount of a compound or a pharmaceutically acceptable salt, ester, stereoisomer, polymorph, solvate, N-oxide, isotopically labeled compound or prodrug thereof, wherein the compound has the following structure:

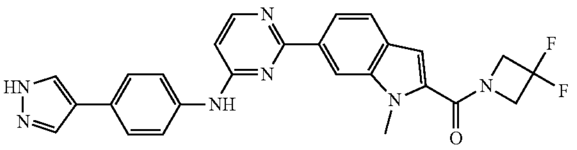 [SMILES: Cn1c(C(=O)N2CC(F)(F)C2)cc2ccc(-c3nccc(Nc4ccc(-c5cn[nH]c5)cc4)n3)cc21]

wherein the subject is a human.

2. The method according to claim 1, wherein the compound or a pharmaceutically acceptable salt, ester, stereoisomer, polymorph, solvate, N-oxide, isotopically labeled compound or prodrug thereof is administered in an amount of 0.005 mg/day to 5000 mg/day.

3. The method according to claim 1, wherein the compound or a pharmaceutically acceptable salt, ester, stereoisomer, polymorph, solvate, N-oxide, isotopically labeled compound or prodrug thereof is administered in an amount of 1 ng/kg to 200 mg/kg, 1 μg/kg to 100 mg/kg or 1 mg/kg to 50 mg/kg body weight per day.

4. The method according to claim 1, wherein the daily dose of the compound or a pharmaceutically acceptable salt, ester, stereoisomer, polymorph, solvate, N-oxide, isotopically labeled compound or prodrug thereof is administered at one time or is administered in two, three or four doses.

5. The method according to claim 1, wherein the compound or a pharmaceutically acceptable salt, ester, stereoisomer, polymorph, solvate, N-oxide, isotopically labeled compound or prodrug thereof is administered continuously for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 1 month, at least 2 months, at least 3 months, at least 4 months, at least 5 months, at least 6 months, at least 1 year, or at least 2 years.

6. The method according to claim 1, wherein the compound or a pharmaceutically acceptable salt, ester, stereoisomer, polymorph, solvate, N-oxide, isotopically labeled compound or prodrug thereof is administered for one or more courses of treatment, wherein each course of treatment lasts for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days or at least 50 days; and the interval between every two courses of treatment is 0, 1, 2, 3, 4, 5, 6, 7, 8, 9, 10 days, two weeks, three weeks, or four weeks.

7. The method according to claim 1, wherein the compound or a pharmaceutically acceptable salt, ester, stereoisomer, polymorph, solvate, N-oxide, isotopically labeled compound or prodrug thereof is administered through injection, or transdermal administration, or is administered via oral, buccal, nasal, transmucosal, topical, as an ophthalmic formulation, or via inhalation.

8. The method according to claim 1, wherein the compound or a pharmaceutically acceptable salt, ester, stereoisomer, polymorph, solvate, N-oxide, isotopically labeled compound or prodrug thereof is administered in a dosage form selected from the group consisting of tablet, capsule, lozenge, hard candy, powder, spray, cream, salve, suppository, gel, paste, lotion, ointment, aqueous suspensions, injectable solution, elixir, and syrup.

9. The method according to claim 2, wherein the compound or a pharmaceutically acceptable salt, ester, stereoisomer, polymorph, solvate, N-oxide, isotopically labeled compound or prodrug thereof is administered in an amount of 0.005, 0.05, 0.5, 5, 10, 20, 30, 40, 50, 100, 150, 200, 250, 300, 350, 400, 450, 500, 550, 600, 650, 700, 750, 800, 850, 900, 950, 1000, 1500, 2000, 2500, 3000, 3500, 4000, 4500 or 5000 mg/day.

10. The method according to claim 1, wherein the compound or a pharmaceutically acceptable salt, ester, stereoisomer, polymorph, solvate, N-oxide, isotopically labeled compound or prodrug thereof is administered in an amount of 1 μg/kg, 10 μg/kg, 25 μg/kg, 50 μg/kg, 75 μg/kg, 100 μg/kg, 125 μg/kg, 150 μg/kg, 175 μg/kg, 200 μg/kg, 225 μg/kg, 250 μg/kg, 275 μg/kg, 300 μg/kg, 325 μg/kg, 350 μg/kg, 375 μg/kg, 400 μg/kg, 425 μg/kg, 450 μg/kg, 475 μg/kg, 500 μg/kg, 525 μg/kg, 550 μg/kg, 575 μg/kg, 600 μg/kg, 625 μg/kg, 650 μg/kg, 675 μg/kg, 700 μg/kg, 725 μg/kg, 750 μg/kg, 775 μg/kg, 800 μg/kg, 825 μg/kg, 850 μg/kg, 875 μg/kg, 900 μg/kg, 925 μg/kg, 950 μg/kg, 975 μg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg or 300 mg/kg body weight per unit dose.

11. The method according to claim 6, wherein the compound or a pharmaceutically acceptable salt, ester, stereoisomer, polymorph, solvate, N-oxide, isotopically labeled compound or prodrug thereof is administered for 1, 2, 3, 4, 5, 6, 7, 8, 9 or 10 courses of treatment.

12. The method according to claim 7, wherein the compound or a pharmaceutically acceptable salt, ester, stereoisomer, polymorph, solvate, N-oxide, isotopically labeled compound or prodrug thereof is administered through intravenous, intraarterial, subcutaneous, intraperitoneal, or intramuscular injection.

13. The method according to claim 12, wherein the compound or a pharmaceutically acceptable salt, ester, stereoisomer, polymorph, solvate, N-oxide, isotopically labeled compound or prodrug thereof is administered through dripping injection.

* * * * *